(12) United States Patent
Heske et al.

(10) Patent No.: US 7,645,239 B2
(45) Date of Patent: Jan. 12, 2010

(54) COAXIAL CANNULA PROVIDED WITH A SEALING ELEMENT

(75) Inventors: Norbert Heske, Kottgeisering (DE); Thomas Heske, Grafrath (DE)

(73) Assignee: C. R. Bard, Inc., Murray Hill, NJ (US)

( * ) Notice: Subject to any disclaimer, the term of this patent is extended or adjusted under 35 U.S.C. 154(b) by 381 days.

(21) Appl. No.: 10/549,820

(22) PCT Filed: Mar. 29, 2004

(86) PCT No.: PCT/EP2004/003327

§ 371 (c)(1),
(2), (4) Date: Sep. 20, 2005

(87) PCT Pub. No.: WO2004/086977

PCT Pub. Date: Oct. 14, 2004

(65) Prior Publication Data

US 2006/0229528 A1      Oct. 12, 2006

(30) Foreign Application Priority Data

Mar. 29, 2003    (DE) ............................ 203 05 093 U

(51) Int. Cl.
*A61B 10/00* (2006.01)
(52) U.S. Cl. ........................ 600/567; 600/564
(58) Field of Classification Search .............. 600/564, 600/567
See application file for complete search history.

(56) References Cited

U.S. PATENT DOCUMENTS

| | | | |
|---|---|---|---|
| 3,606,878 A | 9/1971 | Kellogg, Jr. | |
| 3,844,272 A | 10/1974 | Banko | |
| 4,490,137 A | 12/1984 | Moukheibir | |
| 4,940,061 A | 7/1990 | Terwilliger et al. | |
| 4,958,625 A | 9/1990 | Bates et al. | |
| 5,025,797 A | 6/1991 | Baran | |
| 5,125,413 A | 6/1992 | Baran | |
| 5,282,476 A | 2/1994 | Terwilliger | |
| 5,368,045 A | 11/1994 | Bates et al. | |
| 5,400,798 A | 3/1995 | Baran | |
| 5,526,822 A | 6/1996 | Burbank et al. | |
| 5,546,957 A | 8/1996 | Heske | |
| 5,617,874 A | 4/1997 | Baran | |
| 5,649,547 A | 7/1997 | Ritchart et al. | |
| 5,655,542 A | 8/1997 | Weilandt | |
| 5,709,697 A | 1/1998 | Ratcliff et al. | |

(Continued)

FOREIGN PATENT DOCUMENTS

DE    4041614    10/1992

(Continued)

*Primary Examiner*—Max Hindenburg
*Assistant Examiner*—Michael C Stout

(57) ABSTRACT

A coaxial cannula for extracting samples from tissue having a biopsy needle unit provided with a space for sample extraction and a sample separation unit that coaxially encompasses the biopsy needle on an external wall and that is longitudinally movable. The coaxial cannula includes a sealing element that is arranged on the proximal end thereof and closes the space between the internal wall of the coaxial cannula and the external wall of the sample separation unit. The sealing element opens an air outlet when the biopsy needle unit is inserted, and prevents air intake when the biopsy needle unit is positioned and vacuum is produced in the internal chamber of the biopsy needle.

1 Claim, 4 Drawing Sheets

U.S. PATENT DOCUMENTS

| | | | |
|---|---|---|---|
| 5,718,237 A * | 2/1998 | Haaga | 600/564 |
| 5,752,923 A | 5/1998 | Terwilliger | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,788,651 A | 8/1998 | Weilandt | |
| 5,807,282 A | 9/1998 | Fowler | |
| 5,817,034 A | 10/1998 | Milliman et al. | |
| 5,823,970 A | 10/1998 | Terwilliger | |
| D403,405 S | 12/1998 | Terwilliger | |
| 5,857,982 A | 1/1999 | Milliman et al. | |
| 5,913,857 A | 6/1999 | Ritchart et al. | |
| 5,928,164 A | 7/1999 | Burbank et al. | |
| 5,944,673 A | 8/1999 | Gregoire et al. | |
| 5,951,490 A | 9/1999 | Fowler | |
| 5,964,716 A | 10/1999 | Gregoire et al. | |
| 5,971,939 A | 10/1999 | Cooper et al. | |
| 5,976,164 A | 11/1999 | Mueller et al. | |
| 5,980,469 A | 11/1999 | Burbank et al. | |
| 6,007,495 A | 12/1999 | Matula | |
| 6,007,497 A | 12/1999 | Huitema | |
| 6,019,733 A | 2/2000 | Farascioni | |
| 6,022,324 A | 2/2000 | Skinner | |
| 6,027,458 A | 2/2000 | Janssens | |
| 6,033,369 A * | 3/2000 | Goldenberg | 600/567 |
| 6,036,657 A | 3/2000 | Milliman et al. | |
| 6,050,955 A | 4/2000 | Bryan et al. | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |
| 6,106,484 A | 8/2000 | Terwilliger | |
| 6,110,129 A | 8/2000 | Terwilliger | |
| 6,120,462 A | 9/2000 | Hibner et al. | |
| 6,126,617 A | 10/2000 | Weilandt et al. | |
| 6,142,955 A | 11/2000 | Farascioni et al. | |
| 6,162,187 A | 12/2000 | Buzzard et al. | |
| 6,162,203 A * | 12/2000 | Haaga | 604/272 |
| 6,165,136 A | 12/2000 | Nishtala | |
| 6,193,673 B1 | 2/2001 | Viola et al. | |
| 6,196,978 B1 | 3/2001 | Weilandt et al. | |
| 6,213,957 B1 | 4/2001 | Milliman et al. | |
| 6,221,029 B1 * | 4/2001 | Mathis et al. | 600/564 |
| 6,231,522 B1 | 5/2001 | Voegele et al. | |
| 6,241,687 B1 | 6/2001 | Voegele et al. | |
| 6,273,861 B1 * | 8/2001 | Bates et al. | 600/567 |
| 6,273,862 B1 | 8/2001 | Privitera et al. | |
| 6,280,398 B1 | 8/2001 | Ritchart et al. | |
| 6,283,925 B1 | 9/2001 | Terwilliger | |
| 6,290,476 B1 * | 9/2001 | Wu | 417/549 |
| 6,322,523 B2 | 11/2001 | Weilandt et al. | |
| 6,328,701 B1 | 12/2001 | Terwilliger | |
| 6,402,701 B1 | 6/2002 | Kaplan et al. | |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdoff et al. | |
| 6,436,054 B1 | 8/2002 | Viola et al. | |
| 6,488,636 B2 | 12/2002 | Bryan et al. | |
| 6,514,215 B1 * | 2/2003 | Ouchi | 600/564 |
| 6,540,694 B1 | 4/2003 | Van Bladel et al. | |
| 6,540,761 B2 | 4/2003 | Houser | |
| 6,551,255 B2 | 4/2003 | Van Bladel et al. | |
| 6,554,779 B2 | 4/2003 | Viola et al. | |
| 6,638,235 B2 | 10/2003 | Miller et al. | |
| 6,752,768 B2 | 6/2004 | Burdorff et al. | |
| 6,758,824 B1 | 7/2004 | Miller et al. | |
| 6,764,495 B2 | 7/2004 | Lee et al. | |
| 6,849,080 B2 | 2/2005 | Lee et al. | |
| 7,156,836 B2 * | 1/2007 | Teo | 604/508 |
| 2001/0007925 A1 | 7/2001 | Ritchart et al. | |
| 2001/0011156 A1 | 8/2001 | Viola et al. | |
| 2001/0012919 A1 | 8/2001 | Terwilliger | |
| 2001/0014779 A1 | 8/2001 | Lubock et al. | |
| 2001/0047183 A1 | 11/2001 | Privitera et al. | |
| 2002/0016555 A1 | 2/2002 | Ritchart et al. | |
| 2002/0045840 A1 | 4/2002 | Voegele et al. | |
| 2002/0045842 A1 | 4/2002 | Van Bladel et al. | |
| 2002/0068878 A1 | 6/2002 | Jassoni et al. | |
| 2002/0082519 A1 | 6/2002 | Miller et al. | |
| 2002/0120212 A1 | 8/2002 | Ritchart et al. | |
| 2002/0151822 A1 | 10/2002 | Burdoff et al. | |
| 2002/0156395 A1 | 10/2002 | Stephens et al. | |
| 2003/0088153 A1 * | 5/2003 | Carrillo et al. | 600/114 |
| 2003/0093058 A1 * | 5/2003 | Siang Teo | 604/506 |
| 2003/0199753 A1 * | 10/2003 | Hibner et al. | 600/411 |
| 2004/0186393 A1 | 9/2004 | Leigh et al. | |
| 2004/0215103 A1 | 10/2004 | Mueller, Jr. et al. | |
| 2004/0249278 A1 | 12/2004 | Krause | |
| 2004/0249307 A1 | 12/2004 | Thompson et al. | |
| 2005/0004492 A1 | 1/2005 | Burbank et al. | |
| 2005/0010131 A1 | 1/2005 | Burbank et al. | |
| 2005/0027210 A1 | 2/2005 | Miller | |
| 2005/0165328 A1 | 7/2005 | Heske et al. | |
| 2007/0032741 A1 | 2/2007 | Hibner et al. | |

FOREIGN PATENT DOCUMENTS

| | | |
|---|---|---|
| DE | 10034297 | 4/2001 |
| DE | 10026303 | 2/2002 |
| DE | 20209523 | 9/2002 |
| EP | 0433717 | 6/1991 |
| EP | 0890339 | 1/1999 |
| EP | 0995400 A1 | 4/2000 |
| EP | 1074271 | 2/2001 |
| GB | 2018601 | 10/1979 |
| WO | WO 96/28097 | 9/1996 |
| WO | WO 98/25522 | 6/1998 |
| WO | WO 00/30546 | 6/2000 |
| WO | WO 00/59378 | 10/2000 |
| WO | WO 02/32318 A1 | 4/2002 |
| WO | WO 02/069808 A2 | 9/2002 |

* cited by examiner

COAXIAL CANNULA PROVIDED WITH A SEALING ELEMENT

CROSS-REFERENCE TO RELATED APPLICATIONS

This application is a 35 U.S.C. §371 application of International Application No. PCT/EP04/03327, filed Mar. 29, 2004, which claims priority to German Patent Application No. 20305093.2, filed Mar. 29, 2003, the entireties of which are hereby incorporated by reference.

BACKGROUND OF THE INVENTION

Known from DE GMS 202 09 525.8 is a coaxial cannula that can be inserted into tissue and in which a biopsy needle unit can be employed. A seal is provided between the interior wall of the coaxial cannula and the exterior wall of the biopsy needle unit in order to, first, prevent fluid from escaping and, second, to make it possible to create a vacuum in the tissue to be biopsied. DE GMS 202 09 525.8 states that the sealing function of the seal must be created such that it prevents air from entering or escaping and also prevents fluid from escaping.

Such a seal has led to problems in practice. When inserting the biopsy needle unit into the coaxial cannula and during subsequent positioning of the needle unit, the air that has penetrated into the coaxial cannula as a result of the insertion process is sealed in and air bubbles form that cause problems with the ultrasound or MR images made while the needle is being positioned so that precise positioning is not possible due to the air occlusions.

BRIEF SUMMARY OF THE INVENTION

The object of the invention is to solve this problem.

The invention relates to a coaxial cannula that can be employed in tissue, in which for removing tissue are a biopsy needle unit with specimen removal space and a longitudinally movable specimen separating device that coaxially encloses the biopsy needle on the exterior wall, and whereby the coaxial cannula has on its proximal end a sealing element that encloses the space between the interior wall of the coaxial cannula and the exterior wall of the specimen separating device.

The object is attained in that the sealing element releases the air outlet when the needle unit is inserted and prevents air from entering after the needle unit has been positioned and a vacuum has been created in the biopsy needle interior space.

Due to such an embodiment of the seal, on the one hand air that has been compressed by inserting the needle unit can escape so that no occluded air bubbles are formed and ultrasound or MR images are not affected or disrupted.

The use of an appropriately dimensioned hose that is placed over the proximal end of the coaxial hose is a simple, inexpensive, yet effective embodiment of the sealing element. Care should be taken that the flexibility of the hose is such that during insertion the suction effect at slight underpressure securely closes the gap present between the interior wall of the coaxial cannula and the exterior wall of the needle unit. Specifically, this is attained by using suction to draw the proximal end, e.g., the interior edge, of the hose against the exterior side of the needle unit. For this reason the proximal end of the hose is preferably slightly curved toward the needle unit so that when the vacuum is created the projecting part of the hose piece is drawn inward and pressed against the exterior surface of the needle unit. Removing the vacuum, the underpressure, in the needle hollow space cancels the sealing effect and the gap reopens due to the elasticity of the hose.

However, the sealing element can also be part of the vacuum biopsy device (e.g., in accordance with DE GMS 202 04 363), in particular when the biopsy device is equipped with a guide roller. In this case a stopper on the distal side at the guide roller is provided that acts as a sealer to engage a corresponding coupling bore in the cap of the coaxial cannula. If the sealing elements do not enter into the counterpart until just prior to the device being placed onto the counterpart into the countercoupling parts, the air can exit first. Thus, the effect does not occur until just before the closing so that no air bubbles or air occlusions disrupt the ultrasound or MR images.

If an intermediate piece is used between the guide roller and the proximal surface of the coaxial cap to reduce the penetration depth of the biopsy needle unit, the intermediate piece has one coupling piece on the distal side and one on the proximal side so that the stopper of the guide roller can, first, act as a seal, and second, the intermediate piece can act as a seal in the coupling cap. What is important is that the intermediate space between the needle unit and the coaxial cannula is not closed until just prior to the final positioning of the needle unit so that the air can escape and is not compressed.

BRIEF DESCRIPTION OF THE DRAWINGS

Exemplary embodiments are described in detail as follows.

DETAILED DESCRIPTION OF THE INVENTION

Figure 1:
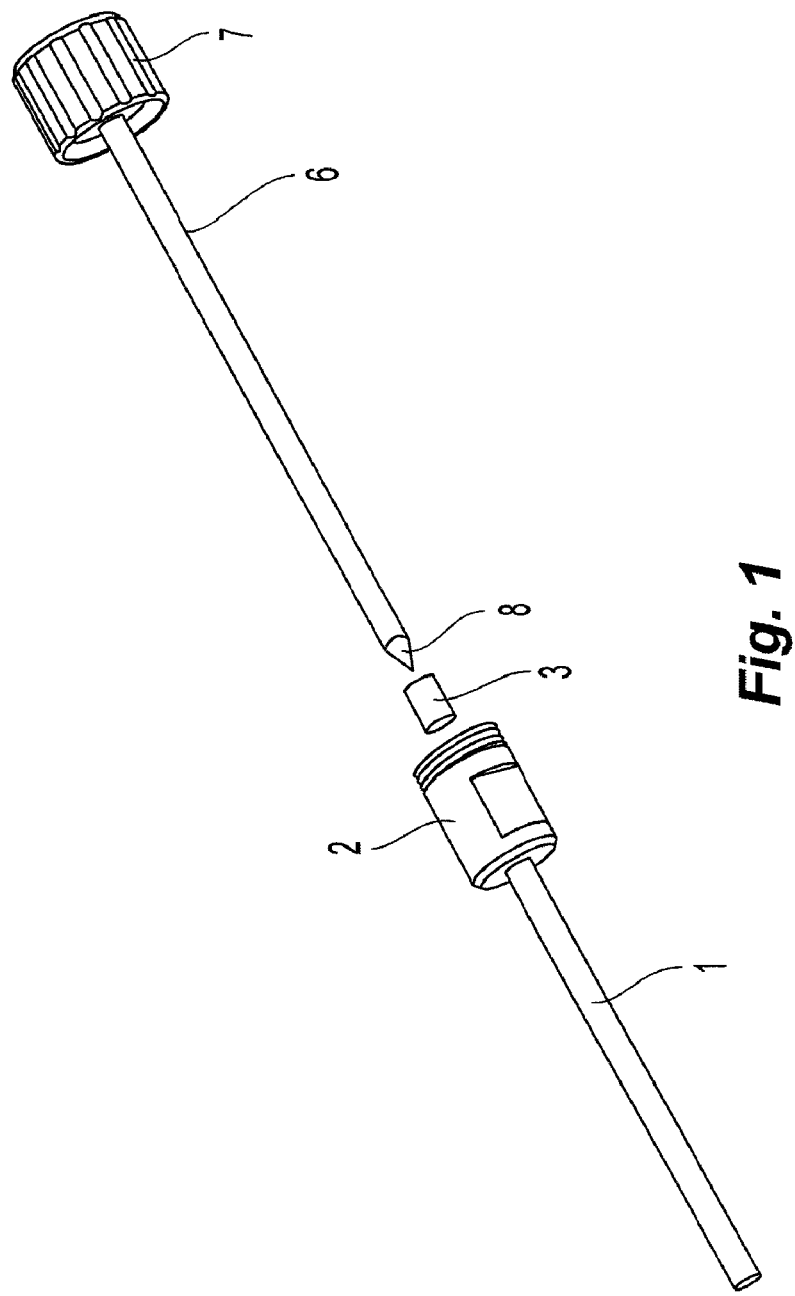
FIG. 1) Exploded depiction of a coaxial cannula with mandrel
Figure 2:
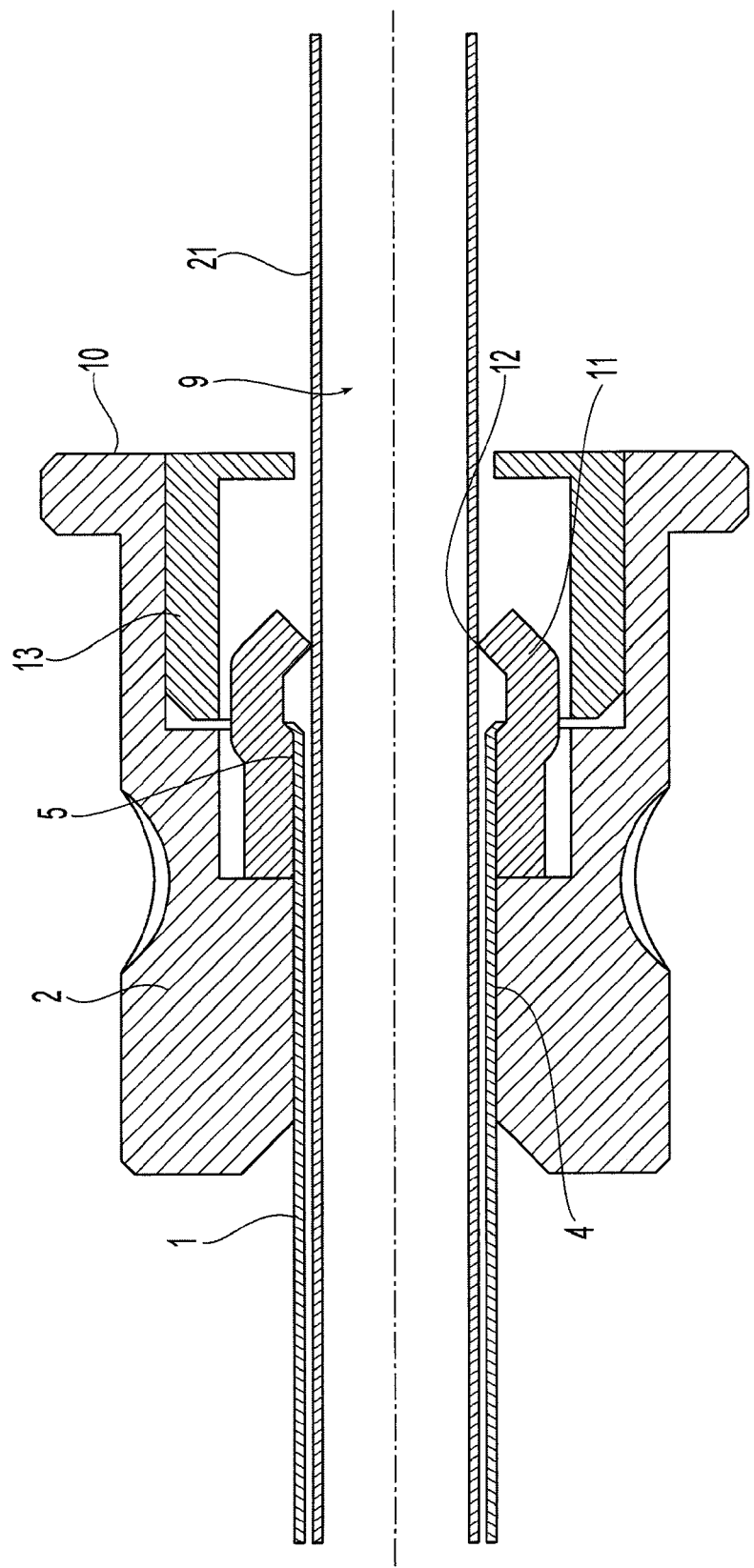
FIG. 2) Section through the cap of a coaxial cannula (variant A, enlarged)

FIG. 1 illustrates a coaxial cannula with mandrel in an exploded drawing. A cap 2 is connected to the coaxial cannula tube 1 ("tube" for short). For attaching the tube 1, the latter projects into an interior bore 4 of the cap 2 at its proximal end 5 into the cap (FIG. 2). For example, a clamping seat holds the proximal tube end 5 in the cap. A sealing element 3, e.g., a hose piece, is placed over the proximal tube end 5. For inserting the coaxial cannula into the tissue, a mandrel 6 (press-in mandrel) is inserted into the coaxial cannula and the mandrel cap 7 is screwed to the cap 2. When assembled, the mandrel tip 8 projects beyond the distal end of the tube.

The coaxial cannula is inserted together with the mandrel into the tissue, e.g., by pressing it in, specifically such that, for example by means of ultrasound equipment, the mandrel tip of the mandrel is guided to or placed in the vicinity of the tissue to be examined.

Once the coaxial cannula has been inserted by means of the mandrel, the mandrel is withdrawn and removed; e.g., by unscrewing the connection to the proximal end. In order to prevent rotation or a change in the positioned coaxial cannula, surfaces are provided on the coaxial cannula in which a fork or clamp that is connected via additional elements engages, e.g., to the operating or examining table, so that the coaxial cannula is held in the selected position.

After the coaxial cannula has been inserted and positioned, and after the mandrel has been removed, the needle unit 9 of a vacuum biopsy device with or without an externally arranged cutting sleeve 21 (specimen separating device) is inserted into the tube 1 of the coaxial cannula (FIG. 2). The needle unit 9 comprises, for example, a hollow needle with a cutting sleeve 21 that encloses it coaxially and has a cutting edge on the distal side. However, the needle apparatus can also be an exterior hollow needle in the hollow space of which the cutting device is coaxially arranged. Instead of the mandrel cap, now the end face, for example of a sterile guide roller 13 of the vacuum biopsy equipment, sits against the proximal end face 10 of the cap 2 (see also FIGS. 3 and 4). After insertion, the end face of the guide roller 13 of the vacuum biopsy device sits on the end face 10 of the cap. When the needle unit is inserted, the air that penetrated after the removal of the mandrel can at first escape until the sealing lip 11 is drawn to the exterior surface of the needle unit by a vacuum created in the hollow needle; i.e., the part of the sealing element that projects beyond the cannula tube on the proximal side is designed so that when the needle unit is inserted a slight gap remains open between the sealing lip and the exterior surface of the needle unit; this occurs, for instance, by having only one edge 12 of the sealing lip touch the exterior surface. When a vacuum is created in the hollow space of the biopsy needle, the underpressure increases the pressure force so that the sealing lip 11, that is, the free hose end, is pressed against the exterior surface of the needle unit, thus preventing the entry of more air.

Figure 3:
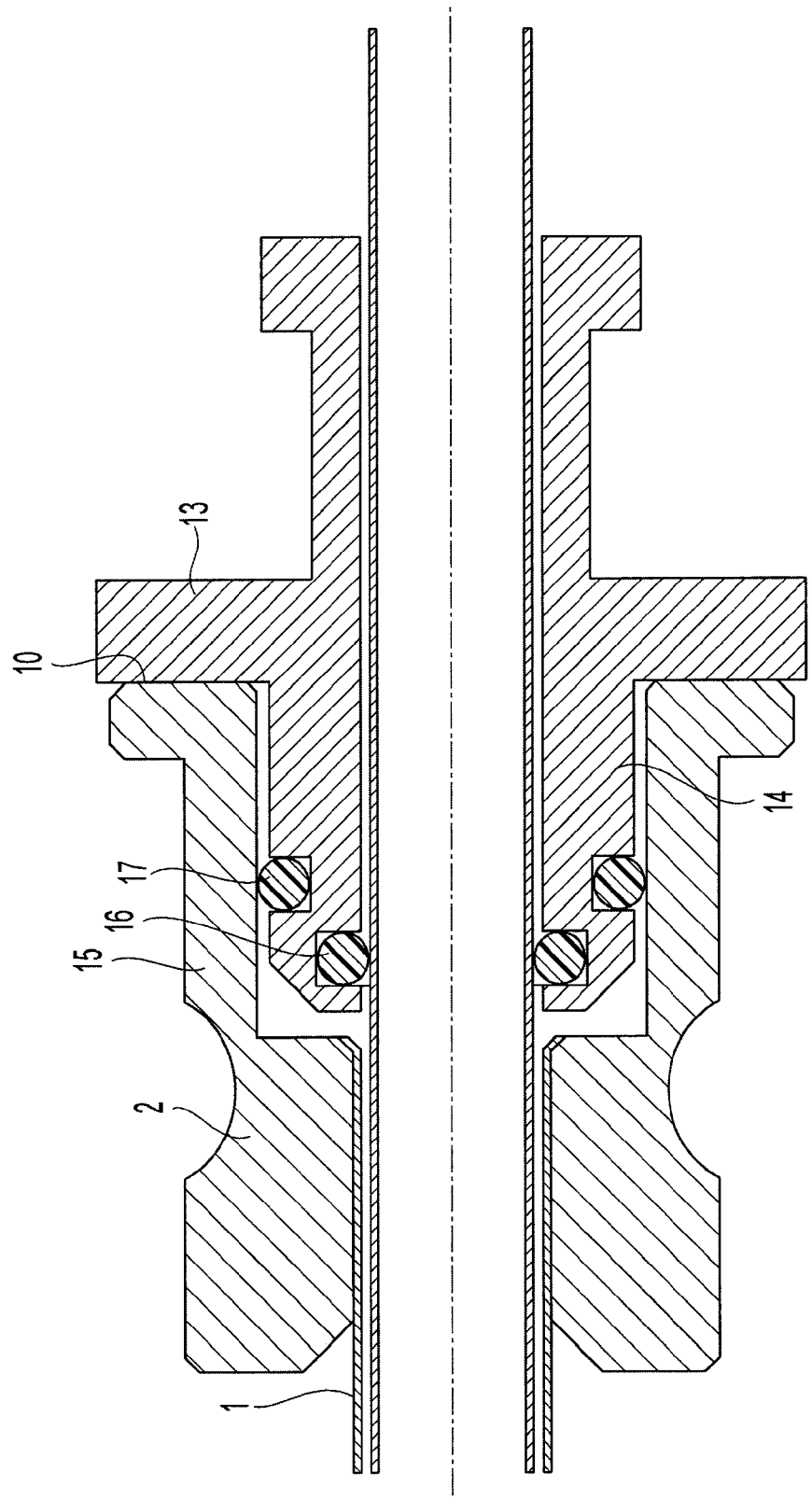
FIG. 3) Section through the cap of a coaxial cannula acting together with a guide roller on the biopsy device (variant B, enlarged)
Figure 4:
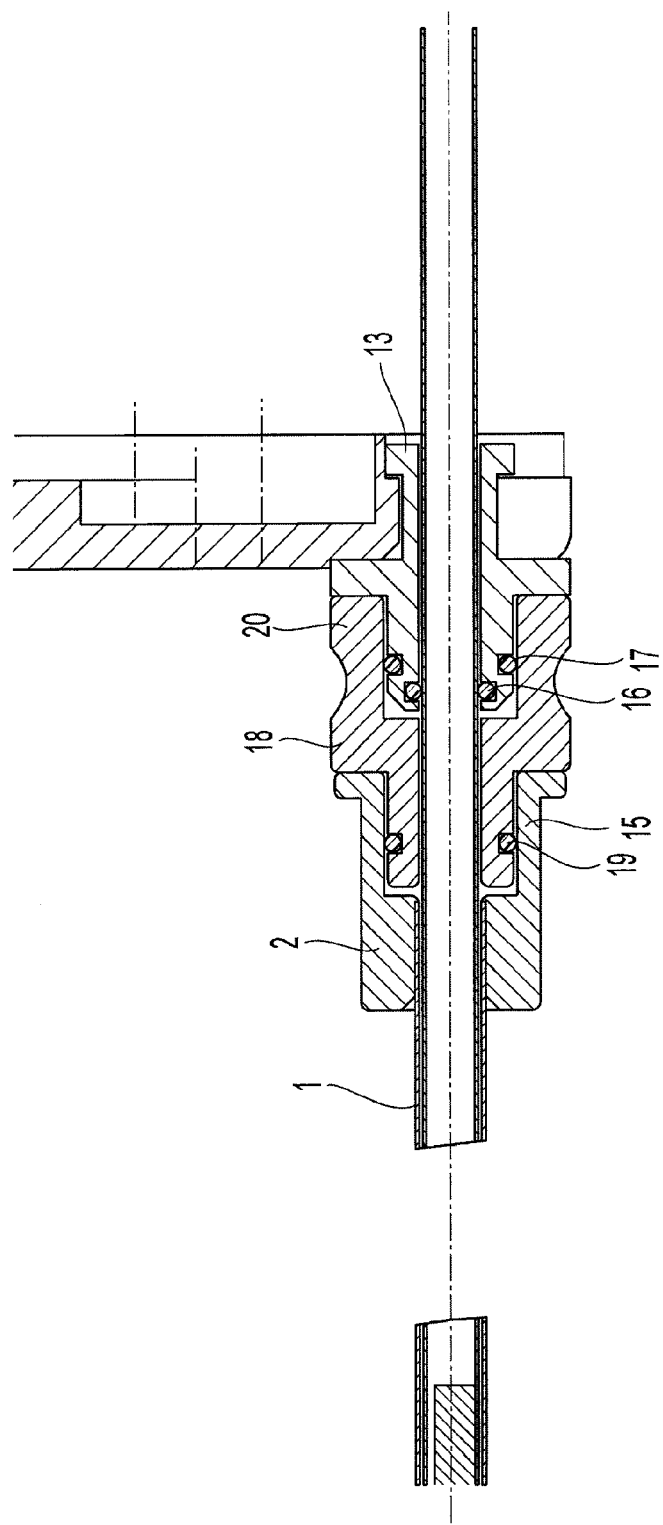
FIG. 4) Section through the coaxial cannula cap using an intermediate piece and a guide roller on the vacuum biopsy device

In the examples illustrated in FIGS. 3 and 4, alternatives for the embodiment of the sealing function, the guide roller 13 does not sit flush with the end face 10 of the cap, and there is also no sealing element arranged on the proximal end of the tube 1, but instead the guide roller of the biopsy device has a stopper 14 that is inserted into a coupling counterpart 15 provided in the cap 2. The stopper seals the exterior surface of the needle unit against the guide roller via the seal 16. The cap is sealed against the stopper of the guide roller by means of the seal 17. Both seals are designed, for example, as O-rings. Because the stopper is kept very short in its longitudinal extension (e.g. stopper length is 5 mm), the sealing effect does not occur until just prior to placing the guide roller on the cap. In other words, the sealing effect does not occur until just before the needle tip is positioned. Air that is present in the coaxial cannula can escape until the sealing effect occurs. FIG. 4 illustrates the same arrangement as FIG. 3, but in this case in order to reduce the penetration depth of the needle unit an intermediate piece 18 is inserted between cap 2 and guide roller 13. The intermediate piece has on its distal side a stopper 14 that is inserted into the coupling counterpiece. The seal between the cap-side coupling counterpiece of the coaxial cannula and the stopper 14 occurs via the seal 19. The stopper 14 of the guide roller is the same as that already described (FIG. 3) and is inserted into a coupling counterpiece 20 of the intermediate piece 18, which is arranged on the proximal side. The sealing arrangement is the same as that described for FIG. 3. In this case, as well, the sealing effect does not occur until just before the tip of the needle unit is brought into its final position. This means that the air that has penetrated can escape from the hollow cannula during the insertion process. The intent of both solutions is that the air that has penetrated into the coaxial cannula when the mandrel is exchanged for the needle unit can escape to the greatest extent possible when the needle unit is inserted so that no disruptions occur during the use of ultrasound or MR.

The invention claimed is:

1. A biopsy apparatus, comprising:
    a coaxial cannula configured for insertion in tissue with the aid of a mandrel, the coaxial cannula having a proximal end and an interior wall;
    a biopsy needle unit configured for insertion into the coaxial cannula after the mandrel is removed from the coaxial cannula, the biopsy needle unit having an exterior wall, an interior space, and a longitudinally movable specimen separating device; and
    a sealing element positioned on the proximal end of the coaxial cannula, the sealing element being configured to enclose an intermediate space between the interior wall of the coaxial cannula and the exterior wall of the biopsy needle unit, wherein the sealing element is configured to provide an air outlet of the intermediate space when the biopsy needle unit is inserted into the coaxial cannula and is configured to prevent air from entering the intermediate space after the needle unit has been positioned and a vacuum has been created in the interior space of the biopsy needle,
    wherein the sealing element is an elastic member defining a sealing lip and having an interior diameter, the sealing element being pushed over the proximal end of the coaxial cannula, the interior diameter being dimensioned to leave open a gap between the sealing lip of the sealing element and the biopsy needle unit, and the elasticity of the sealing element is such that, given an underpressure in the intermediate space between the exterior wall of the biopsy needle unit and the interior wall of the coaxial cannula, the sealing lip of the sealing element at the gap comes into contact with the biopsy needle unit to form a seal against the biopsy needle unit.

* * * * *